(12) United States Patent
Kaur et al.

(10) Patent No.: US 6,485,971 B1
(45) Date of Patent: Nov. 26, 2002

(54) KERATINOCYTE STEM CELLS

(75) Inventors: Pritinder Kaur; Paul J. Simmons, both of East Melbourne (AU)

(73) Assignee: Peter MacCallum Cancer Institute, Victoria (AU)

( * ) Notice: Subject to any disclaimer, the term of this patent is extended or adjusted under 35 U.S.C. 154(b) by 0 days.

(21) Appl. No.: 09/664,437

(22) Filed: Sep. 18, 2000

Related U.S. Application Data

(63) Continuation of application No. PCT/AU99/00177, filed on Mar. 18, 1999.

(30) Foreign Application Priority Data

Mar. 18, 1998 (AU) .............................................. PP 2444

(51) Int. Cl.$^7$ .............................. C12N 5/08; C12N 5/00; C12N 5/02
(52) U.S. Cl. ...................... 435/371; 435/325; 435/366; 435/378; 435/395
(58) Field of Search ................................ 435/325, 378, 435/366, 371, 395

(56) References Cited

U.S. PATENT DOCUMENTS 6,165,514 A * 12/2000 Bockman et al. ........... 424/495

OTHER PUBLICATIONS

James G. Rheinwald, et al., Serial Cultivation of Strains of Human Epidermal Keratinocytes: the Formation of Keratinizing Colonies from Single Cells, Nov. 1975, Cell, vol. 6, pp. 331–344.

R. J. Morris, et al. Slowly cycling (label–retaining) epidermal cells behave like clonogenic stem cells in vitro, 1994, Cell Proliferation 27, pp. 279–289.

Rebecca J. Morris, et al., Evidence That the Centrally and Peripherally Located Cells in the Murine Epidermal Proliferative Unit Are Two Distinct Cell Populations, 1985, The Journal of Investigative Dermatology, vol. 84, No. 4, pp 277–281.

Ian C. Mackenzie, et al., Isolation of subpopulations of murine epidermal cells using monoclonal antibodies against differentiation–related cell surface molecules, 1989, Differentiation 41, pp. 127–138.

I. C. Mackenzie, et al., Label–retaining keratinocytes and Langerhans cells in mouse epithelia, 1985, Cell and Tissue Research pp. 551–556.

L. G. Lajtha, Stem Cell Concepts, 1979, Differentiation 14, pp. 23–24.

Elaine Fuchs, et al. Changes in Keratin Gene Expression during Terminal Differentiation of the Keratinocyte, 1980, Cell, vol. 19, pp. 1033–1042.

Ennó Christophers, M.D. Cellular Architecture of the Stratum Corneum, 1971, The Journal of Investigative Dermatology, vol. 56, No. 3, pp. 165–169.

T.D. Allen, et al., Fine–Structural Identification and Organization of the Epidermal Proliferative Unit, 1974, T Cell Science 15, pp. 291–319.

Jones, P.H., Isolation and characterization of human epidermal stem cells, Clinical Science (1996) 91, 141–146.

Bickenbach, Jackie, et al., Selection and Extended Growth of Murine Epidermal Stem Cells in Culture, Experimental Cell Research 244, 184–195 (1998) Article No. EX984163.

Kaur, Printinder, et al., Identification of a Cell Surface Protein with a Role in Stimulating Human Keratinocyte Proliferation, Expressed During Development and Carcinogenesis, The Journal of Investigative Dermatology, vol. 109, No. 2, Aug. 1997.

Bickenbach, J.R., et al., Rate of loss of tritiated thymidine label in basal cells in mouse epithelial tissues, Cell Tissue Kinet. (1986) 19. 325–333.

Li, Amy, et al, Identification and isolation of candidate human keratinocyte stem cells based on cell surface phenotype, Proc. Natl. Acad. Sci. USA, vol. 95, pp 3902–3907, Mar. 1998.

Baum, Charles M., et al., Isolation of a candidate human hematopoietic stem–cell population, Proc. Natl. Acad. Sec. USA, vol. 89, pp. 2804–2808, Apr. 1992, Cell Biology.

Berenson, Ronald J., et al., Engraftment After Infusion of $CD34^+$ Marrow Cells in Patients With Breast Cancer or Neuroblastoma, Blood, vol. 77, No. 8 (Apr. 15), 1991: pp 1717–1722.

Carter, William G., et al., The Role of Integrins $\alpha 2\beta 1$ and $\alpha 3\beta 1$ in Cell–Cell and Cell–Substrate Adhesion of Human Epidermal cells, The Journal of Cell Biology, vol. 110, Apr. 1990 1387–1404.

Carter, William G., et al., Distinct Functions For Integrins $\alpha 3\beta 1$ in Focal Adhesions and $\alpha 6\beta 4$/Bullous Pemphigoid Antigen in a New Stabel Anchoring Contact (SAC) of Keratinocytes: Relation to Hemidesmosomes, The Journal of Cell Biology, vol. 111 (No. 6, Pt. 2), Dec. 1990, 3141–3154.

(List continued on next page.)

Primary Examiner—Remy Yucel
Assistant Examiner—Katharine F Davis
(74) Attorney, Agent, or Firm—Sughrue Mion, PLLC

(57) ABSTRACT

Enrichment for human Keratinocyte Stem Cells KSCs to a high degree of purity can be successfully achieved on the basis of a cell surface component whose expression is proliferation-related in conjunction with an integrin such as the $\alpha_6\beta_4$ integrin. Transferrin receptor may be used as the cell surface component that is proliferation related. Enrichment of Transit amplifying cells can also be achieved by use of a variation of this method. The enrichment follows on from harvesting of cells from an epithelium, preferably rich in stem cells.

32 Claims, 9 Drawing Sheets

OTHER PUBLICATIONS

Civin, Curt I., et al., Antigenic Analysis of Hematopoiesis, III. A Hematopoietic Progenitor Cell surface Antigen Defined by a Monoclonal Antibody Raised against KG–la Cells[1], The Journal of Immunology, vol. 133, Jul. 1984, pp. 157–165.

Dowling, James, et al., β4 Integrin Is Required for Hemidesmosome Formation, Cell Adhesion and Cell Survival, The Journal of Cell Biology, vol. 134, No. 2, Jul. 1996 559–572.

Georges–Labouesse, Elisabeth, et al., Absence of integrin α6 leads to epidermolysis bullosa and neonatal death in mice, Nature Genetics, vol. 13, Jul. 1996, pp. 370–373.

Grieder, Carol W., Telomerase activity, cell proliferation, and cancer, PNAS Online, vol. 95, Issue 1, 90–92, Jan. 6, 1998.

Haylock, D.N., et al., Ex Vivo Expansion and Maturation of Peripheral Blood CD34$^+$ Cells Into the Myeloid Lineage, Blood, vol. 80, No. 6 (Sep. 15), 1992: pp. 1405–1412.

Haylock, David N., et al., Increased Recruitment of Hematopoietic Progenitor Cells Underlies the Ex Vivo Expansion Potential of FLT3 Ligand, Blood, vol. 90, No. 6 (Sep. 15), 1997: pp. 2260–2272.

Hiyama, Keiko, et al., Activation of Telomerase in Human Lymphocytes and Hematopoietic Progenitor Cells[1], The Journal of Immunology, 1995, 155: 3711–3715.

Hurlin, Peter J., Progression of human papillomavirus type 18–immortalized human keratinocytes to a malignant phenotype, Proc. Natl. Acad. Sci. USA, vol. 88, pp. 570–574, Jan. 1991, Cell Biology.

Jones, Philip H., et al, Stem Cell Patterning and Fate in Human Epidermis, Cell, vol. 80, 83–93, Jan. 13, 1995.

Jones, Philip H., et al., Separation of Human Epidermal Stem Cells from Transit Amplifying Cells o the Basis of Differences n Integrin Function and Expression, Cell, vol. 73, 713–724, May 21, 1993.

Kim, Nam W., et al., Specific Association of Human Telomerase Activity with Immortal Cells and Cancer, Science, vol. 266, Dec. 23, 1994, pp. 2011–2015.

Morris, Rebecca J., et al., Evidence That a Slowly Cycling Subpopulation of Adult Murine Epidermal Cells Retains Carcinogen[1], Cancer Research 46, 3061–3066, Jun. 1986.

Peltonen, Juha, et al., Localization of Integrin Receptors for Fibronectin, Collagen, and Laminin in Human Skin, Variable Expression in Basal and Squamous Cell Carcinomas, vol. 84, Dec. 1989, 1916–1923.

Potten, Christopher S., Clonogenic cells and stem cells in epidermis, Int. J. Biol., 1973, vol. 24, No. 5, 537–540.

Potten, C.S., et al., Cell Cycles in cell hierarchies, Int. J. Radiat. Biol., vol. 49, No. 2, 257–278.

Schofield, R., The Relationship Between the Spleen Colony–forming Cell and the Haemopoietic Stem Cell, Blood Cells 4, 7–25 (1978).

Schweizer, Jürgen, et al., Sequential Expression of mRNA–Encoded Keratin Sets in Neonatal Mouse Epidermis: Basal Cells with Properties of Terminally Differentiating Cells.

Sonnenberg, Arnoud, et al., Integrin α6β4 Complex is Located in Hemidesmosomes, Suggestin a Major Role in Epidermal Cell–Basement Membrane Adhesion, The Journal of Cell Biology, vol. 113, No. 4, May 1991 907–917.

Spangrude, Gerald J., Purification and Characterization of Mouse Hematopoietic Stem Cells, Science, vol. 24, pp. 58–62.

Sutherland, Heather J., et al., Functional characterization of individual human hematopoietic stem cells cultured at limiting dilution on supportive marrow stromal layers, Proc. Natl. Acad. Sci. USA, vol. 87, pp. 3584–3588, May 1990, Medical Sciences.

Terstappen, Leon W.M.M., et al., Sequential Generatins of Hematopoietic Colonies Derived From Single Nonlineage–Committed CD34$^+$CD38$^-$ Progenitor Cells, Blood, vol. 77, No. 6 (Mar. 15), 1991:pp 1218–1227.

Van Der Neut, Ronald, et al., Epithelial detachment due to absence of hemidesmosomes in integrin β4 null mice, Nature Genetics, vol. 13, Jul. 1996, pp. 366–369.

Bata–Csorgo, Zs., et al., Flow Cytometric Identification of Proliferative Subpoputaions within Normal Human Epidermis and the Localization of the Primary hyperproliferative Population is Psoriasis, J.Exp. Med., vol. 178, Oct. 1993, 1271–1281.

* cited by examiner

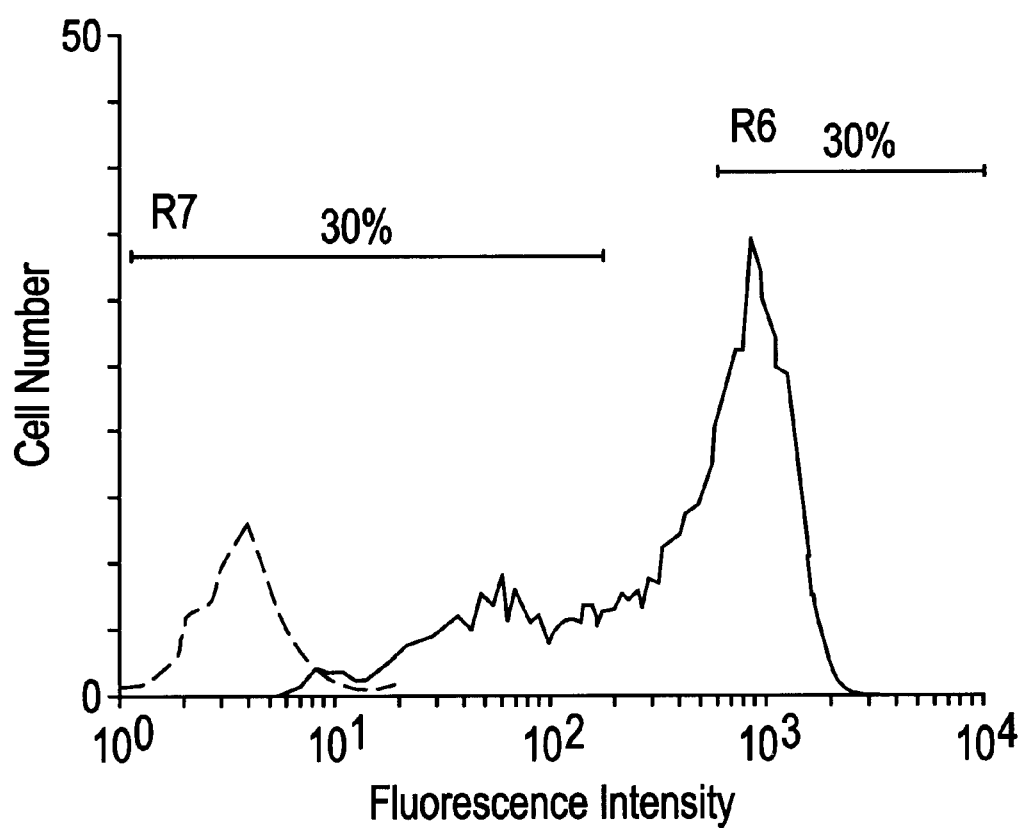

| FRACTIONS | NUMBERS OF COLONIES ± SEM |
|---|---|
| UF | 19.67 ± 1.33 |
| $\alpha_6^{dim}$ (R7) | 3.0 ± 1.15 |
| $\alpha_6^{bri}$ (R4) | 21 ± 3.06 |
| $\alpha_6^{bri} 10G7^{bri}$ (R2) | 15.67 ± 0.33 |
| $\alpha_6^{bri} 10G7^{dim}$ (R3) | 20.67 ± 2.03 |

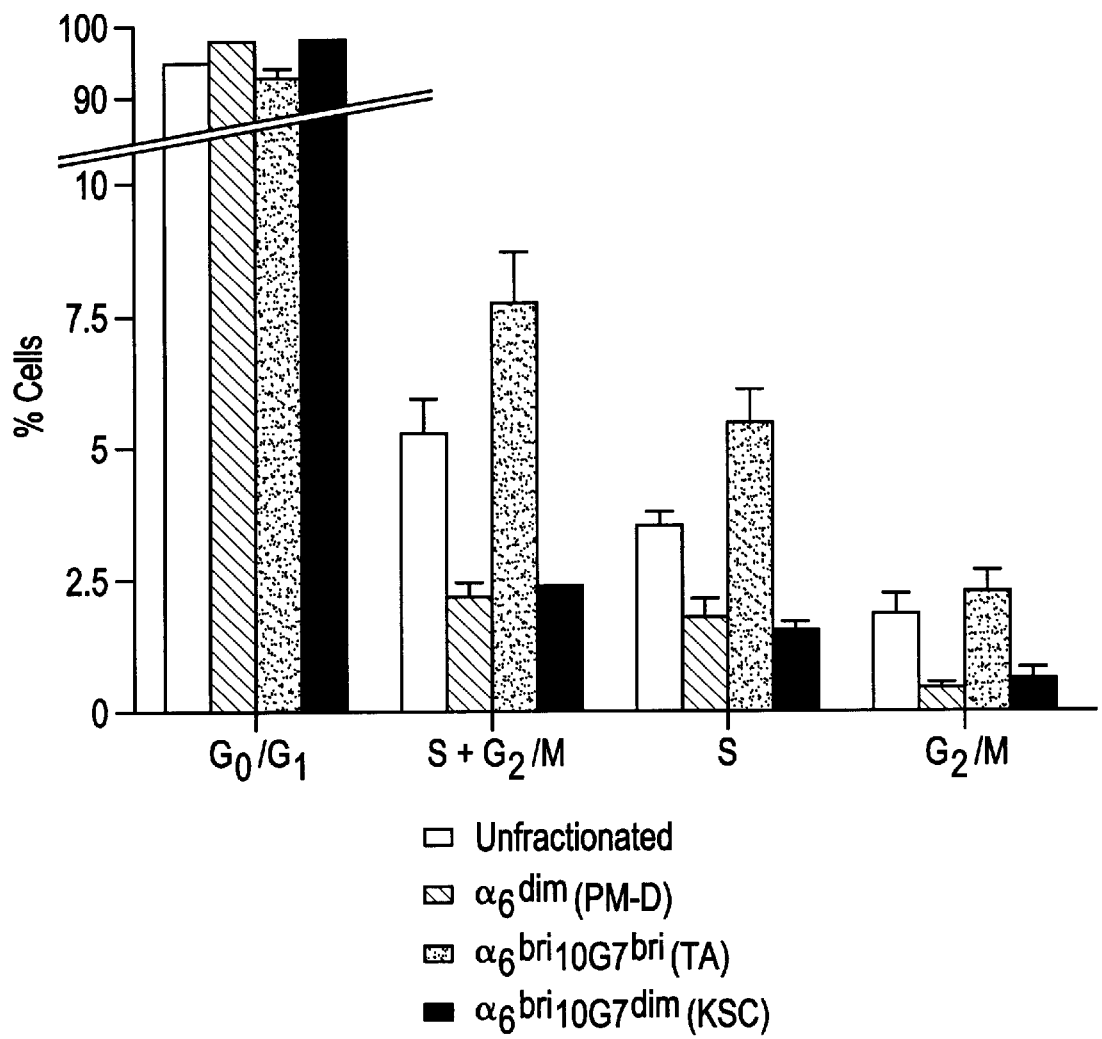

KERATINOCYTE STEM CELLS

CROSS REFERENCE TO RELATED APPLICATIONS

This is a Continuation of PCT Application No. PCT/AU99/00177, filed Mar 18, 1999, which claims benefit of priority based on Australian Application No. PP2444, filed Mar. 18, 1998.

This invention relates to a method of enriching for and isolating subpopulations of epithelia cells, isolation of keratinocyte stem cells, to keratinocyte stem cells and uses for keratinocyte stem cells.

BACKGROUND OF THE INVENTION

In common with other rapidly renewing tissues such as the haemopoietic system and the intestinal epithelia, the human epidermis is in a process of constant regeneration. Terminally differentiated cells lost continuously from the skin surface, are replaced by an intricate and highly regulated proliferative process within the basal layer of the epidermis. Stem cells in these rapidly renewing tissues are the earliest progenitors of a hierarchy of proliferative cells which are ultimately responsible for the generation of all mature cells for the lifetime of an individual (Lajtha, 1979). In murine epidermis, this process is achieved by two kinetically distinct subpopulations: (a) keratinocyte stem cells (KSC) which represent a minor subpopulation of relatively quiescent cells, defined by their great proliferative potential and an unlimited capacity for self renewal, identified as slow-cycling, $^3$H-Tdr label-retaining cells; and (b) transit amplifying (TA) cells—the progeny of the stem cells, with a limited proliferative capacity identified as a pool of rapidly proliferating cells that are lest from the basal layer to terminal differentiation within 4–5 days (Potten, 1983: Morris et al, 1985; MacKenzie & Bickenbach, 1985; Potten, 1986; Bickenbach et al, 1986). In addition, a third Subpopulation of basal keratinocytes representing post-mitotic differentiating cells in the early stages of keralinisation can also be identified (Potten, 1983; Morris et al, 1985; MacKenzie & Bickenbach, 1985; Potten, 1986; Bickenbach et al, 1986; Christophers, 1971; Allen & Potten, 1974). Human epidermis has similar populations.

Given that all proliferative activity in the human epidermis is restricted to the basal layer, this is presumably where the stem cells and TA cells reside. It has also been established that the hair follicle can act as an important reservoir of epidermal stem cells, and that cells within the bulge region have extensive proliferative potential. Physiological cell renewal in interfollicular epidermis however, is most likely to be achieved by stem cells and TA cells within the basal layer. However there are no molecular markers that distinguish between basal keratinocytes that have made a commitment to differentiate (TA cells) and immature stem cells.

In the haemopoietic system, multilineage reconstituting stem cells can be physically separated from committed progenitor cells (analogous to the TA cells of the epidermis). based upon differences in their expression of cell surface markers (Civin et at, 1984; Spangrude et al, 1988; Berenson et al, 1991; Terstappen et al, 1991; Baum et al, 1992). Clearly the availability of appropriate cell surface markers on basal epidermal cells would greatly facilitate the isolation and characterisation of human KSCs. However, the cell surface antigenic phenotype of these cells remains relatively poorly defined.

One of the best studied classes of cell surface molecules expressed by keratinocytes are the integrin superfamily of cell adhesion receptors. Integrins are heterodimeric cell surface glycoproteins that primarily mediate the attachment of basal keratinocytes to extracellular matrix proteins found in the basement membrane, but can also mediate intercellular adhesion. In vivo, basal keratinocytes express the $\beta_1$ integrins $\alpha_3\beta_1$ and as well as the integrin $\alpha_6\beta_4$ (Peltonen et at, 1989; Carter et al, 1990a Carter et al, 1990b). Important evidence for proliferative heterogeneity in human basal keratinocytes has been provided by recent work using a fluorescence activated cell sorting (FACS) approach, demonstrating that both cultured and primary human foreskin keratinocytes could be separated into cells with high levels of $\beta_1$ integrin ($\beta_1$ bright) which had a high plating efficiency assayed after two weeks in culture, compared to those keratinocytes with low levels of this integrin (Jones & Watt, 1993; Jones et al, 1995). Furthermore, bright keratinocytes were shown to be capable of generating an epithelial sheet when grafted onto mice, suggesting that this fraction of the basal layer contain KSCs (Jones et al, 1995).

In vivo studies suggest that epidermal stem cells constitute between 1%–10% of the basal layer depending on the methodology used (Morris et al, 1985; MacKenzie & Bickenbach, 1985; Bickenbach et al, 1986; Potten & Hendry, 1973; Morris & Potten, 1994). Since approximately 40% of the basal layer in human foreskin exhibits high levels of $\beta_1$ integrin in vim (Jones et at, 1995) it is highly likely that basal keratinocytes with this phenotype contain both the KSC population and a significant number of TA cells and therefore there are drawbacks in the use of cells enriched for high level expression of $\beta_1$.

OBJECT OF THE INVENTION

An object of one aspect of the invention is to generate a more purified population of keratinocyte stem cells than has been achieved by prior art methods. An object of a further aspect of the present invention is to provide methods for purifying subpopulations of epithelial cells.

SUMMARY OF THE INVENTION

A strategy for distinguishing between the TA cells and the KSCs of the epidermis based on the use of two cell surface antigens has been shown to be effective. In view of functional data demonstrating the role of integrin $\alpha_6\beta_4$ in mediating adhesion of basal keratinocytes to the basement membrane via hemi-desmosomes (Sonnenberg et al, 1991; Dowling et at, 1996; Georges-Labouessee et al, 1996; Vander-Neut et al, 1996) it was hoped that this integrin may provide a suitable marker for epidermal stem cells since these cells are permanently anchored to the basement membrane.

It is now shown that while basal keratinocytes expressing low levels of $\alpha_6\beta_4$ represent a subpopulation of post-mitotic, differentiating keratinocytes, this integrin is expressed at high levels on both the KSC and TA cells. Thus this cell surface marker alone, cannot be used to separate KSCs from TA cells to a high degree of purity but can do so to a degree of purity higher than where $\beta_1$ integrin is used.

It is the finding of the inventors that enrichment for human KSCs to a high degree of purity can be successfully achieved on the basis of a second cell surface component whose expression is proliferation-related in conjunction with $\alpha_6\beta_4$ integrin. The experiments conducted to date have used transferrin receptor as the cell surface component that is proliferation related. It is also suggested that sufficient purification should be achievable where another marker capable of identifying KSC and TA cells (and perhaps also cells that have been differentiated further) is used in place of $\alpha_6\beta_4$ in the above two step process and that other marker might be another integrin such as $\alpha_2\beta_1$ or $\alpha_3\beta_1$.

In a first aspect the invention could be said to reside in a method of enriching a viable population of KSCs from a population of epidermal cells comprising, a) a first enriching step of enriching for cells carrying a high level of cell surface integrin from the population of epidermal cells to form a partially enriched pool, and b) a second enriching step of removing cells that carry high level expression of a marker associated with proliferation from the partially enriched pool.

Conversely TA cells might be purified from KSCs whereby a proportion of cells with low expression of a marker associated with proliferation are removed from the partially enriched pool.

The epidermal cell population might be derived (torn a tissue sample of the skin. This method normally involves the separation of epidermis from the skin sample, before the enrichment. One particularly good source of KSC cells is from the basal layer of the epidermis. The proportion of these cells that are KSCs will depend upon the type of skin, and the age of the individual concerned. It is estimated for example that about 10% of neonatal foreskins are KSC cells but a lesser proportion will be present in the basal layer of the epithelium of adults. Hair follicles are also known to be a reservoir of stem cells and might be used as a source rich in KSCs.

It has been shown that significant enrichment can be achieved in the first step by the use of $\beta_1$ in the first enrichment step, and it is thus thought that integrins $\alpha_2\beta_1$ or $\alpha_3\beta_1$ could be used in this enrichment. $\beta_1$ is however less effective in the two step enrichment process than $\alpha_6\beta_4$ integrin because it recognises epidermal cells that have developed past the TA stage and therefore the first enrichment step leads to a lesser enrichment than by use of $\alpha_6\beta_4$ integrin which recognises only KSC cells and TA cells.

The marker associated with proliferation that has been used by the inventors is one that is recognised by monoclonal antibody 1007 and has now been identified as being the transferrin receptor. There are a number of commercially available monoclonal antibody preparations that also recognise transferrin receptor. Alternative markets that are associated with proliferation can also be used examples of these include but are not limited to the EGF (Epidermal Growth Factor) receptor, and perhaps also the IGF (Insulin Growth Factor) receptor and the KGF (Keratinocyte Growth Factor) receptor.

It will be understood recognition of cells carrying the cell surface markers that form the basis of the separation can be effected by a number of different methods, however, all of these methods rely upon binding of a binding agent to the integrin molecule, followed by a separation of chose that have high levels of binding from those that have low levels of binding. The most convenient binding agents are antibodies or antibody based molecules, preferably being monoclonal antibodies or based on monoclonal antibodies because of the specificity of these latter agents. Antibodies can be used for both steps. However other agents might also be used, thus ligands for these integrins such as extracellular matrix proteins including laminin-5 or collagen I or IV may also be employed to enrich for cells carrying $\alpha_6\beta_4$. Likewise transferrin itself could be used as a means for detecting the levels of transferrin receptor, in place of 10G7 or other antibody directed against transferrin receptor.

The antibodies may be attached to a solid support to allow for crude separation. The separation techniques employed should maximise the retention of viability of the fraction to be collected. Various techniques of different efficacy may be employed to obtain relatively crude separations. The particular technique employed will depend upon efficiency of separation, associated cytoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to, FACS.

In the experiments conducted thus far the $\alpha_6\beta_4$ has been selected on the basis of the portion being identified, i.e. $\alpha_6$, however the $\beta_4$ portion could equally well be used. Commercially available monoclonal antibody preparations that recognise $\alpha_6$ are available for these for example those known as GOH3 and 4F10.

It is found that by using an accurate separation method a purified KSC cell population can be achieved, which is believed to have less than 1% non KSC cells, however using cruder enrichment techniques a variety of levels of purified KSC cells can be produced, and may be useful at lower levels of purity. It is believed that purity levels of greater than 50% or at least greater than 70% may be useful for an improved formation of an epidermal layer which can be used as a graft for a skin lesion. A substantially purified KSC cell population of greater than about 90% is thought to be useful for not only the formation of an epidermal layer but also for use as a starting cell population for genetic modification whereby exogenous nucleic acid is introduced to express a desired product, which may be used in gene therapy.

In this regards it is considered that enriching for KSCs on the basis of the presence of $\beta_1$ alone integrin will result in a population with only a limited capacity to provide a differentiated skin graft, it is suggested that selection of the $\alpha_6\beta_4$ on its own may result in a sufficiently pure population of KSC cells to achieve an enhanced capacity to produce a differentiated epidermal layer. With a higher purity of KSCs it is expected that a graft should repopulate faster and should persist longer.

The capacity to isolate substantially purified KSCs opens up significant useful potential in some quite major areas.

Firstly autologous repair of skin lesions, by the formation of a layer of skin generated from cells isolated from the same individual. Methods of generating epidermis from epidermal cells are found for example in U.S. Pat. No. 5,712,163 by Parenteau et al which also refers to other references therein, particularly in column one which are incorporated herein by reference. It is suggested that these methods will be applicable where KSCs and TA cells of the present invention are used.

Secondly the accessibility of skin makes KSCs an ideal candidate for generic manipulation and gene therapy for the treatment of both skin disorders and systemic deficiencies. Thus exogenous nucleic acid would be introduced into autologous KSCs, to produce a therapeutically useful substance. The cells can be formed into an epidermal layer which could be grafted onto the skin of the individual concerned and act as a means for long term release of the therapeutic compound. The compound is thus introduced systemically. The compound might be one that is not produced by the individual as a result of a congenic defect, or a disorder that has developed, for example diabetes. Purification of KSCs according to the present invention are suggested to give rise to a skin graft of greater persistence and accordingly the gene therapy should last longer than would otherwise be possible. Suggestions for gene therapy using KSCs for gene therapy have been made with one of the acknowledged deficiencies being recognised as the lack of purified KSCs.

A third useful result of this invention relates to the enhanced capacity to find markers associated with proliferation of various cell sub populations of the skin involved in the early proliferative events and to enhance the understanding of these early proliferative events, with the greater potential to discover the reason for defects in the proliferative process which lead to cancers.

The invention could therefore also be said to reside in a composition including an enriched cell population of KSC cells capable of being enriched by firstly enriching a cell population for cells that carry an integrin marker and secondly reducing the number of cells that carry a marker associated with proliferation. Such compositions might include a tissue layer suitable for autologous skin graft application and a genetically modified population of KSC cells.

In a further form the invention could be said to reside in a composition formed from an enriched cell population of KSC of this invention. The composition could be the result of an epidermal layer that is used as a skin graft that has been derived from KSCs.

BRIEF DESCRIPTION OF THE DRAWINGS

FIGS. 1A and 1B: Fractionation and colony forming ability of neonatal primary human foreskin basal epidermal cells on the basis of $\alpha_6$ integrin expression.

FIG. 1A: Flow cytometric analysis of freshly isolated basal keratinocytes stained with either an anti-$\alpha_6$ Mab (4F10 solid line) or isotype control Mab (ID4.5-broken line), detected by a FITC-conjugated secondary antibody. Two fractions representing the upper 30% (R6) $\alpha_6^{bri}$ cells and the lower 30% (R7) $\alpha_6^{dim}$ cells were collected by FACS and cultured.

FIG. 1B: Colony numbers obtained from 5000 UF, $\alpha_6^{bri}$ and $\alpha_6^{dim}$ cells. Keratinocyte colony numbers were determined after two weeks in culture, by staining with toluidine blue after removal of the feeder layers. The $\alpha_6^{bri}$ fraction consistently gave rise to greater colony numbers that the $\alpha_6^{dim}$ fraction, indicating than the $\alpha_6^{bri}$ fraction was enriched for colony forming cells. These results are typical of several replicate experiments (n=5).

FIG. 2A: Growth curves of the UF cells, $\alpha_6^{bri}$ and the $\alpha_6^{dim}$ fractions in a representative experiment are shown. Each point represents the mean cell output±SEM of three replicate wells obtained at each passage. The curves show that the $\alpha_6^{bri}$ cells consistently grew at a greater rate than the UF cells and the $\alpha_6^{dim}$ fraction. The inset shows growth curves from day 0–50 to illustrate cell proliferation during this period, not evident on the main graph due to the scale. These results are typical of several replicate experiments (n=5).

FIG. 2B: The total cell output (cumulative cell yield), from 5000 cells of each fraction, was determined at the end of the experiment when their ability to proliferate was exhausted. The total cell output of the $\alpha_6^{bri}$ fraction was significantly higher than the $\alpha_6^{dim}$ fraction and UF cells (p<0.05), thus confirming that the $\alpha_6^{bri}$ population had the greatest long term proliferative capacity. The numbers above the columns indicate mean cell yields from each fraction. The results shown represent the mean total output±SEM of three separate experiments.

FIG. 3A: FIG. A shows that both these fractions were positive for the basal keratin K14, but that the $\alpha_6^{dim}$ cells expressed lower levels of K14 than the $\alpha_6^{bri}$ cells.

FIG. 3B: FIG. B shows that the $\alpha_6^{bri}$ fraction was negative for the differentiation-specific keratin K10, while $\alpha_6^{dim}$ cells were positive for this marker. Staining with appropriate isotype-matched negative control Mabs (ID4.5 and IB5) is shown (dotted lines) in each figure.

FIGS. 4A and 4B: Fractionation and colony forming ability of neonatal primary human foreskin basal epidermal cells on the basis of $\alpha_6$ integrin and 10G7 ag expression.

FIG. 4A: Dot plot showing flow cytometric analysis of freshly isolated basal keratinocytes double-labeled with anti-$\alpha_6$ Mab 4F10 (FITC), and Mab 10G7 (PE), from a representative experiment. Four fractions of cells were collected in this experiment: the $\alpha_6$dim population (R7), the $\alpha_6^{bri}$ cells (R4), and the latter cells subdivided on the basis of relatively high (R2, $\alpha_6^{bri}10G7^{bri}$) or low levels (R3, of $\alpha_6^{bri}10G7^{dim}$) of 10G7 ag expression. This phenotype has been observed in numerous replicate experiments (n=25).

FIG. 4B: Colony numbers obtained from 5000 cells from each fraction at two weeks in culture. The $\alpha_6^{bri}10G7^{dim}$ and $\alpha_6^{bri}10G7^{bri}$ fractions consistently gave rise to greater colony numbers than the $\alpha_6^{dim}$ fraction. Importantly no significant difference between colony numbers was obtained from the $\alpha_6^{bri}10G7^{dim}$ and $\alpha_610G7^{bri}$ fractions. These results are typical of several replicate experiments (n=5).

FIG. 5A: Growth curves of UF, $\alpha_6^{bri}10G7^{dim}$ and $\alpha_6^{bri}10G7^{bri}$ fractions in a representative experiment. The curves show that the $\alpha_6^{bri}10G7^{dim}$ cells consistently grew at a greater rate than the UF and $\alpha_6^{bri}10G7^{bri}$ cells. Cell output at earlier time points (Day 0–50) is shown in the inset, and indicates that all fractions were capable of growth in culture, not evident on the main graph due to the scale. Data points represent mean±SEM of three replicates.

FIG. 5B: Total cell output of fractions determined at the end of the experiment, from an initial input of 5000 cells per fraction, confirm that the $\alpha_6^{bri}10G7^{dim}$ population has the greatest long-term proliferative capacity and comprises the candidate keratinocyte stem cell population. The numbers above the columns indicate mean cell yields from each fraction. The data is shown as the mean±SEM of three replicates. These results are typical of several separate experiments (n=5).

FIG. 6: Cell cycle analysis of primary basal keratinocytes fractionated on the basis of $\alpha_6$ and 10G7 ag expression. The UF cells show that overall, the basal layer contains about 5% of cells progressing through the S-phase of the cell cycle. Analysis of fractionated cells clearly demonstrates that the majority of these actively cycling basal cells reside within the candidate TA population ($\alpha_6^{bri}10G^{bri}$ cells), whereas the candidate KSC population ($\alpha_6^{bri}10G7^{dim}$) and the post-mitotic differentiating (PM-D) cells ($\alpha_6^{dim}$ fractions) comprise mostly quiescent cells, with relatively fewer cells in S- or S/G$_2$M phase. The results displayed in this figure are the mean±SEM of four separate experiments.

DETAILED DESCRIPTION OF THE INVENTION

EXAMPLE 1

Figure 2A:
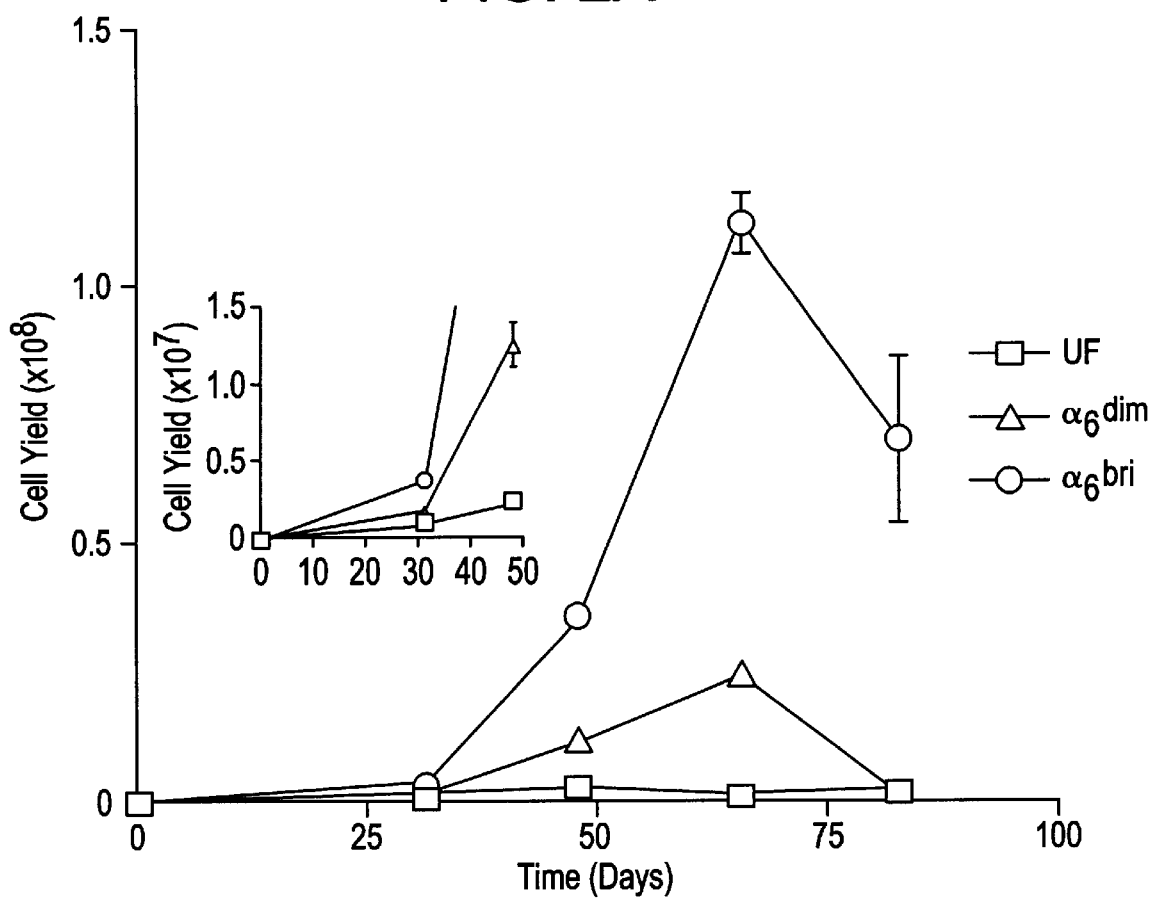
FIGS. 2A and 2B: Long-term growth capacity of $\alpha_6^{bri}$ and $\alpha_6^{dim}$ cells.

Materials & Methods
Isolation and culture of primary basal keratinocytes.

Human neonatal foreskins from routine circumcisions were processed within 2 hours of collection. Epithelial sheets were obtained after overnight incubation with 4 mg/ml. Dispase at 4° C. and basal keratinocytes isolated by trypsinisation for 5 minutes. Keratinocytes were cultured using the Rheinwald and Green method (Rheinwald & Green, 1975), on irradiated Swiss 3T3-J2 feeder layers in DMEM containing 10% FCS, 20 ng/ml epidermal growth factor (Sigma), 0.4 µg/ml hydrocortisone (Sigma), and 10 ng/ml cholera toxin (Calbiochem La Jolla, USA). Keratinocytes were passaged after removing the feeder cells with 0.02% EDTA.
Antibodies.

Mab 4F10 (IgG$_{2a}$) to the $\alpha_6$ integrin subunit was used at 20 µg/ml (Serotec, Oxford, UK); Mab 10G7 (IgG$_{2a}$) developed in our laboratory was used as undiluted hybridoma supernatant. Isotype-matched negative control Mabs 1D4.5 (IgG$_{2a}$), 1B5 (IgG$_1$) and 1A6.11 (IgG$_{2b}$) available in house. And-mouse IgG$_{2b}$-FITC and IgG$_{2a}$-PE (Caltag Laboratories, San Francisco, USA), were used to detect 4F10 and 10G7 binding respectively. Mabs LHP2 (IgG$_1$) to K10 and LL001 (IgG$_{2a}$) to K14 were kindly provided by Dr Irene Leigh (Royal London Hospital, London, UK), and used at 1:10 and 1:1000 respectively.
Immunofluorescence staining and FACS of primary keratinocytes.

Basal keratinocytes were processed for single ($\alpha_6$-FITC) or double ($\alpha_6$-FITC and 10G7 ag)-PE staining along with appropriate negative controls and single colour positive controls to establish compensation settings on the FACS as described previously. (Kaur et al, 1997). The cells were resuspended in culture medium at 2–3×10$^6$/ml, sorted using the Becton-Dickinson FACStar$^{Plus}$ and collected into culture medium. The viability of the cells after sorting was determined to be >95%. Double staining for keratins and $\beta_6$ was performed on cells fixed and permeabilised in 70% ethanol at −20° C. for 10 mins.

Determination of total cell output of fractionated basal cells as an indicator of enrichment for epidermal stem cells.

The KSC population has been defined as a minor subpopulation of the basal layer with greatest proliferative capacity since it must sustain tissue renewal for a lifetime. Based on the assumption that KSCs have a specific cell surface phenotype, as has been demonstrated for bone marrow haemopoietic progenitors, when plating equivalent numbers of cells with the hypothesised KSC phenotype and UF cells, one should clearly expect greater cell output from the former population since it has been enriched for stem cells. At the start of each long term culture experiment, cells fractionated on the basis of their cell surface phenotype were sorted. 5000 keratinocytes from each fraction were plated into 24-well plates containing monolayers of feeder cells. All fractions per experiment were plated in triplicate, carried in parallel and passaged at the same time. The number of cells produced by each fraction was determined at each passage (with the exception of the first passage, where the number of cells are very small), by harvesting the cells and obtaining cell counts. At first passage, cells from each fraction were pooled and plated equally into 3 wells of a 6-well plate. At subsequent passages, all fractions were replated at 5×10$^4$ cells per well of a 6-well plate, in triplicate irrespective of cell yield. The keratinocytes were continually passaged until their growth capacity had been exhausted. The cumulated total cell output of 5000 cells from each fraction was then determined at the end of each experiment. Since only 5×10$^4$ cells were replated at each passage, the cell outputs were calculated assuming all the cells from the previous passage had been replated The duration of each experiment was dependent on the individual keratinocyte cultures, but was generally between 75–95 days.
Cell cycle analysis Fractionated primary basal keratinocytes were collected by FACS, fixed with 70% ethanol (20° C.), and treated with RNAase prior to staining with 40 µg/ml propidium iodide. DNA content was analysed by flow cytometry on an EPICS XL flow cytometer (Couker) within 12 hours.

RESULTS

Given that stem cells may not maintain their in vivo characteristics in culture after removal from their "niche" or microenvironment (Schofield et al, 1978), we elected to analyse freshly isolated primary epidermal cells. We compared the relative proliferative capacity measured as total cell output, following long-term culture of parallel fractions of basal keratinocytes, and the cycling status of these fractions upon isolation from the foreskin, reasoning that by definition, KSCs would be distinguished from TA cells based on well accepted differences attributed to these two populations of proliferative cells, i.e. the KSC subpopulation defined by its relative quiescence in viva and the greatest proliferative potential in vitro; compared to the TA cells characterized by their actively cycling status in vivo, reduced proliferative potential and more rapid terminal differentiation in culture (Lajtha, 1979).
Separation of basal keratinocytes into proliferative cells and post-mitotic differentiating cells based on expression of the $\alpha_6$ integrin.

In accord with published studies on the expression of $\alpha_6\beta_4$ in neonatal human foreskin in vivo. (Carter et al, 1990b) freshly isolated basal keratinocytes were found to be $\alpha_6$ positive by flow cytometric analysis. However, a bimodal pattern of expression was consistently observed (FIG. 1A: n=25). Two fractions of cells, the upper 30% population ($\alpha_6^{bri}$; fluorescence intensity range of 10$^2$–10$^3$) and the lower 30% population ($\alpha_6^{dim}$; fluorescence intensity range of $10^1$–$10^2$), together with unfractionated cells (UF), were compared in culture. The colony forming ability of these primary keratinocytes determined at two weeks (FIG. 1B), in five separate experiments, showed that the $\alpha_6^{bri}$ cells consistently gave rise to greater colony numbers than the $\alpha_6^{dim}$ cells (typically 18.3±0.47 versus 3.33±0.94 respectively), but was not significantly different than UF cells (typically 24.67±6.12), suggesting that the majority of proliferating cells were in the $\alpha_6^{bri}$ fraction.

Figure 2B:
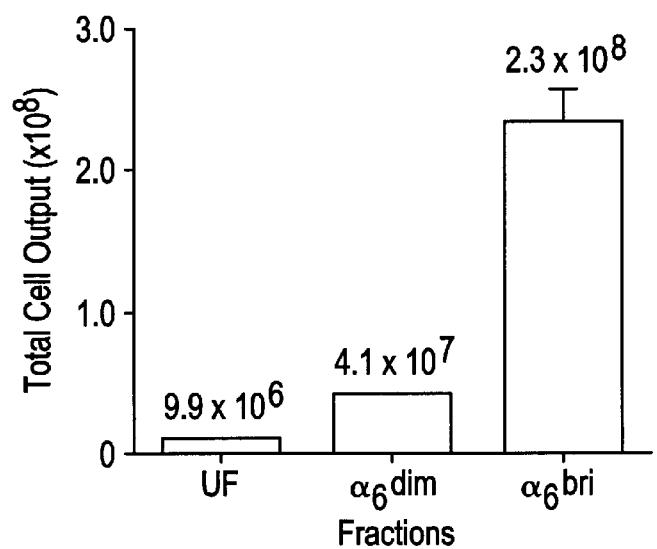

Studies in the haemopoietic system demonstrate that stem cells with marrow repopulating activity do not clone directly in vitro, but will over time in culture give rise, through differentiation, to clonogenic cells (Sutherland et al., 1990; Haylock et al., 1992; Haylock et al., 1997). By analogy, it is possible that the colony forming ability of keratinocytes measured over a two week period may not accurately predict the long-term growth capacity of KSCs. We therefore compared the long-term proliferative capacity of the $\alpha_6^{bri}$ and $\alpha_6^{dim}$ populations by assaying total cell output following serial passage, until all growth potential was exhausted (typically 75–95 days). The data obtained from several separate experiments (n=5), demonstrated clearly that basal cells with the greatest long-term proliferative capacity reside in the $\alpha_6^{bri}$ subpopulation (FIG. 2A and FIG. 2B).

Figure 3A:
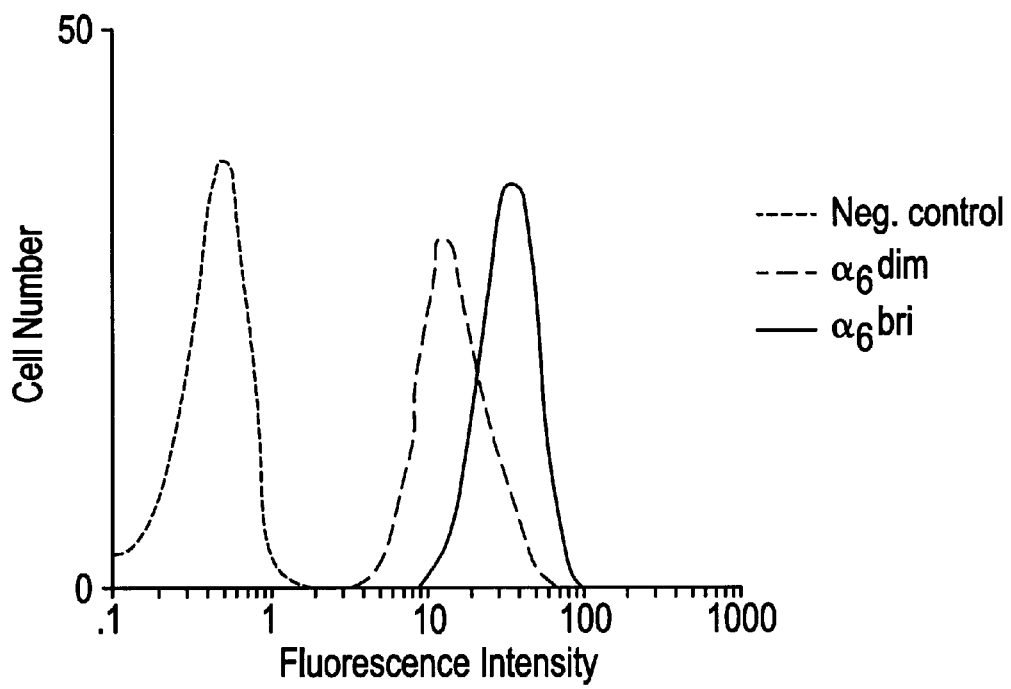
FIGS. 3A and 3B: Two-colour flow cytometric analysis of $\alpha_6$ and keratins 14 and 10 in neonatal primary human foreskin basal epidermal cells. Freshly isolated keratinocytes were fixed, permeabilised and double labeled with anti-$\beta 6$ integrin (Mate 4F10) and either (A) anti-K14 (Mate LL001 or (B) anti-K10 (Mate LHP2). Cells were analysed for keratin expression after gating into $\alpha_6^{bri}$ and $\alpha_6^{dim}$ fractions.
Figure 3B:
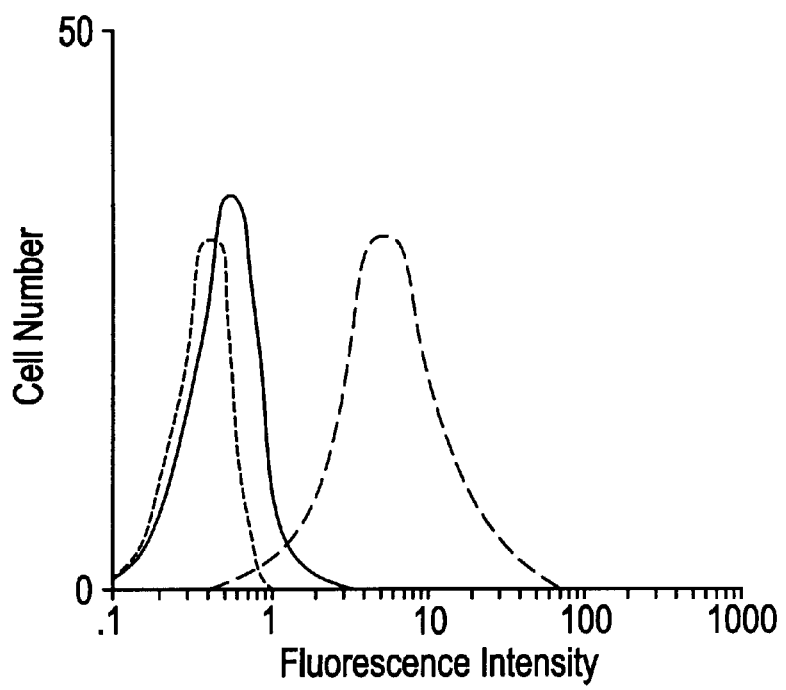

In vivo epidermal cells exhibit ordered expression of pairs of keratins (K). Thus, K5 and K14 are expressed by basal cells, while K1 and K10 are predominantly expressed in the suprabasal differentiating layers of the epidermis (Fuchs & Green. 1980). However, K10 expression has also been observed in a minor subpopulation of basal cells in murine epidermis (Schweizer, 1984; Mackenzie et at, 1989) suggesting the presence of differentiating cells within the basal layer. Flow cytometric analysis demonstrated than both the $\alpha_6^{dim}$ and $\alpha_6^{bri}$ fractions were K14 positive (FIG. 3A), although the $\alpha_6^{dim}$ cells showed significantly lower levels of K14 than $\alpha_6^{bri}$ cells (n=4). In contrasts while the $\alpha_6^{bri}$ keratinocytes were negative for K10, the $\alpha_6^{dim}$ fraction expressed this differentiation marker (FIG. 3B). Collectively, these data demonstrate that the $\alpha_6^{dim}$ fraction comprise a population of post-mitotic differentiating basal cells, while the $\alpha_6^{bri}$ fraction contains the majority of proliferative basal keratinocytes i.e. KSCs and TA cells.

Human epidermal stem cells can be resolved further within the $\alpha_6^{bri}$ population on the basis of 10G7 antigen (transferrin) expression.

In vivo cell kinetic studies have established that KSCs are largely quiescent, and do not proliferate at high rates, while TA cells are actively cycling (Potten, 1983; Morris et al, 1985; MacKenzie & Bickenbach, 1985; Potten, 1986; Bickenbach et al, 1986). We therefore reasoned that these two populations could be distinguished at the time of initial isolation from the epidermis, on the basis of a second proliferation-associated cell surface marker recognized by a monoclonal antibody Mab 10G7, recently generated in our laboratory (Kaur et al, 1997). Mab 10G7 was raised against a previously described tumourigenic human keratinocyte cell line (Hurlin et at, 1991) and recognizes transferrin receptor.

Figures 4, 4A:
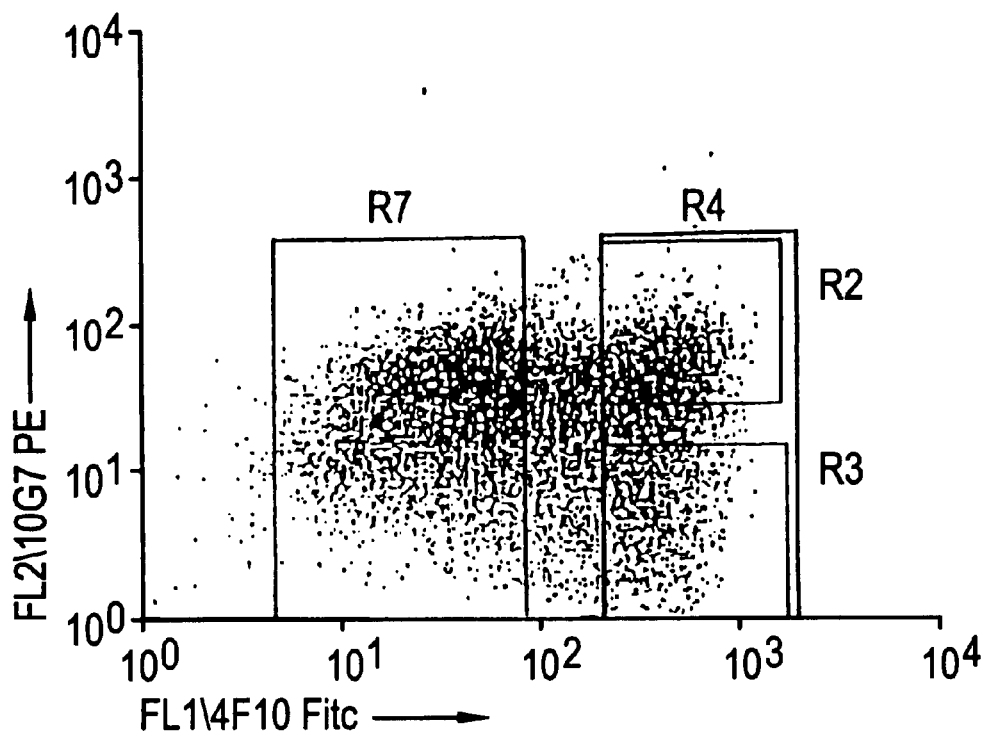
Figure 5A:
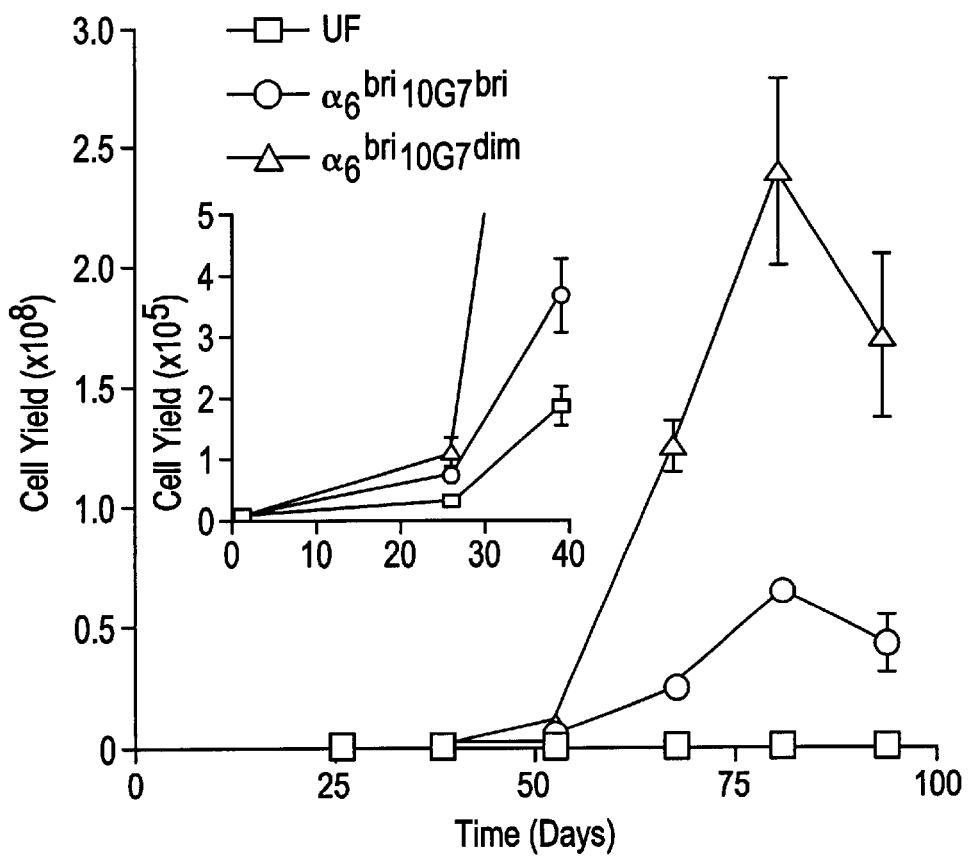
FIGS. 5A and 5B Long-term growth capacity of primary human neonatal foreskin basal epidermal cells fractionated on the basis of $\alpha_6$ and 10G7 ag expression.
Figure 5B:
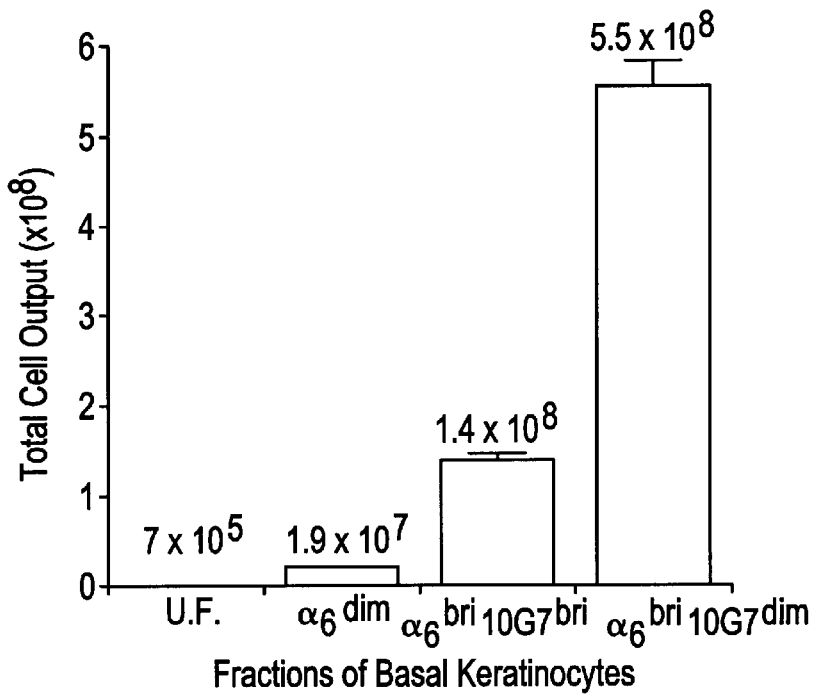
Figure 7:
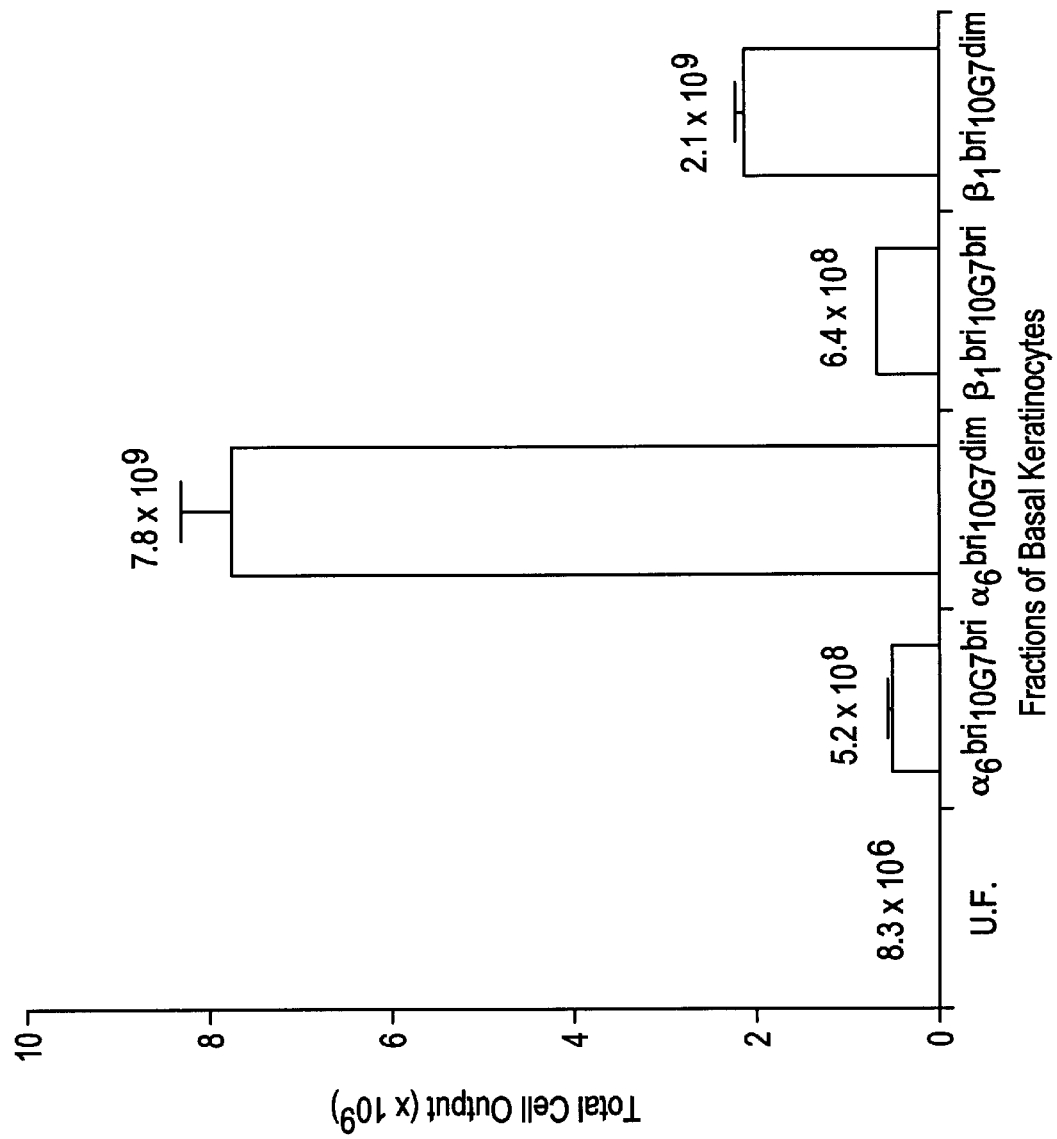
FIG. 7: Total cell output of $\alpha_6^{bri}$ and $\beta_1^{bri}$ further subdivided with Mab 10G7. The values above each bar represent mean cell yield from each fraction.

Flow cytometric analysis of freshly isolated human epidermal basal cells double labeled with Mab 10G7 and anti-$\alpha_6$ integrin antibody, consistently showed that the $\alpha_6^{bri}$ population demonstrated a broad range of 10G7 ag expression with the majority exhibiting relatively high levels of expression and the remainder, low levels (FIG. 4A; n=25). The $\alpha_6^{bri}$ population was separated by FACS into the upper 30% ($\alpha_6$10G7$^{bri}$) and the lower 30% of 10G7 ag expressing cells ($\alpha_6^{bri}$10G7$^{dim}$). The short term proliferative capacity of these fractionated basal keratinocytes was similar (FIG. 4B) as determined by the colony numbers obtained at two weeks, typically 15.67±0.33 versus 20.67±2.03 from the $\alpha_6^{bri}$10G7$^{bri}$ and $\alpha_6^{bri}$10G7$^{dim}$ respectively (n=5). However, these two subpopulations differed markedly in their capacity to sustain long term generation of keratinocytes. The growth curves and total cell outputs from a typical experiment are shown in FIG. 5A and FIG. 5B, and illustrate that the $\alpha_6^{bri}$10G7$^{dim}$ population exhibits a significantly greater proliferative potential than any of the other populations assayed (p<0.05). In this experiment, total cell outputs from 5000 UF, $\alpha_6^{bri}$, $\alpha_6^{bri}$10G7$^{bri}$ or $\alpha_6^{bri}$10G7$^{dim}$ were 7×10$^5$, 1.9×10$^7$, 1.4×10$^8$ and 5.5×10$^8$ respectively. The absolute number of cells generated by a particular fraction in long-term culture was variable between experiments and can be attributed to variation between skin donors, and the duration of the experiment, dictated by the period for which cells from a particular donor could be maintained in culture. However, importantly the $\alpha_6^{bri}$10G7$^{dim}$ fraction consistently contained basal epidermal cells with the greatest total cell output in several replicate experiments (n×5) (see Table 1). Interestingly, the $\alpha_6^{bri}$10G7$^{dim}$ cells exhibited significantly greater rates of growth in culture, particularly between day 50 and 80 compared to the other fractions (FIG. 5A), ultimately resulting in the greatest cumulative cell output of any fraction (FIG. 5B). These data demonstrate that the KSCs can be markedly enriched from the $\alpha_6^{bri}$ fraction of basal keratinocytes, on the basis of 10G7 ag expression, and clearly reside in the $\alpha_6^{bri}$10G7$^{dim}$ fraction.

The candidate keratinocytes stem cell fraction ($\alpha_6^{bri}$10G7$^{dim}$) represents a quiescent subpopulation of the epidermal basal layer.

To investigate the cycling status of the and the $\alpha_6^{bri}$10G7$^{dim}$ and the $\alpha_6^{bri}$10G7$^{bri}$ subpopulations, sorted cells were processed for propidium iodide staining and analysed by flow cytometry. The results obtained from four separate experiments shown in FIG. 6 demonstrate that the majority of actively cycling basal keratinocytes (i.e. cells in S+G$_2$/M phase), reside in the $\alpha_6^{bri}$10G7$^{bri}$ (putative TA) fraction, while $\alpha_6^{bri}$10G7$^{dim}$ basal keratinocytes, designated as the putative KSC fraction contain significantly more quiescent cells (p=0.0004), Basal keratinocytes designated as the post-mitotic differentiating fraction ($\alpha_6^{dim}$) did not contain many cycling cells as expected. These observations are in close accord with published data demonstrating that in vivo, approximately 5% of basal keratinocytes (UF) are engaged in DNA synthesis, (Allen & Potten. 1974) and confirm that the $\alpha_6^{bri}$10G7$^{dim}$ fraction exhibits predicted stem cell characteristics, representing an initially quiescent subpopulation of basal epidermal cells, capable of the greatest regenerative capacity in vivo.

Contrary to our expectation that KSCs may exclusively express high levels of $\alpha_6\beta_4$ integrin to maintain tight adhesion to the basement membrane, our data clearly demonstrate that this integrin is highly expressed on both KSCs and TA cells ($\alpha_6^{bri}$ cells). However, post mitotic basal cells already exhibiting differentiation characteristics, demonstrated lower levels of $\alpha_6$ integrin ($\alpha_6^{dim}$ cells), presumably in preparation for migration into the suprabasal layer. Interestingly, these K10 positive basal keratinocytes were able to demonstrate significant proliferative activity in vitro, indicating that their commitment to differentiate in vivo can be reversed by placing them in culture. This is similar to the in vivo induction of proliferation in suprabasal cells during wound healing.

Basal keratinocytes with the phenotype $\alpha_6 10G7^{dim}$ have important stem cell attributes.

The present strategy for enriching for epidermal stem cells on the basis of a proliferation-related cell surface marker allows for the separation of proliferative basal cells into the quiescent KSC compartment demonstrating the greatest regenerative capacity in long-term culture ($\alpha_6^{bri}10G7^{dim}$) and an actively cycling TA compartment with lesser proliferative capacity ($\alpha_6^{bri}10G7^{bri}$). We estimate that a single candidate KSC with the phenotype $\alpha_6^{bri}10G7^{dim}$ can generate approximately $5.8\times10^8$ cells. It is highly likely that the present culture conditions, while promoting very effective growth of the TA population, do not permit optimal cell generation from or self-renewal of the KSC population.

The present data also show that the candidate KSC fraction represents an immature and minor subpopulation of approximately 10% of the basal layer, consistent with estimates of 1–10% from kinetic studies in murine epidermis (Morris et al, 1985; MacKenzie & Bickenbach, 1985; Potten, 1986: Bickenbach et al, 1986; Potten & Hendry 1973). Given that we have used neonatal human foreskin tissue which is capable of greater proliferation than adult foreskin epithelium (Rheinwald & Green, 1975), it is likely that these KSC numbers are higher than may be found in adult epidermis.

Previous reports suggest that enrichment of KSCs can be achieved by selecting cells expressing high levels of $\beta_1$ integrin (Jones & Watt, 1993; Jones et al, 1995). Work in our own laboratory indicates that both the KSC and TA fractions express high levels of $\beta_1$ and $\alpha_6$ integrins. In addition, we have observed that the selection of $\alpha_6^{bri}10G7^{dim}$ cells allows the isolation of greater numbers of putative stem cells than $\beta_1^{bri}10G7^{dim}$ cells (Kaur & Li, submitted). Our data suggests that this can probably be attributed to the fact that while the majority of basal keratinocytes express high levels of both of these integrins, there is a significant subpopulation of $\beta_1^{bri}$ cells that express low levels of $\alpha_6$ ($\alpha_6^{dim}$ post-mitotic, differentiating cells).

It is noteworthy that the TA compartment remains indistinguishable from the KSC compartment at present due to the absence of very early differentiation markers. Clearly, our ability to recognize this population phenotypically, will permit us to Investigate the molecular differences between these two populations. This work will provide a basis for the identification of genes with a critical role in epidermal growth and differentiation, and factors regulating self-renewal of KSCs. Further, it has important implications for the study of epidermal carcinogenesis, given that the stem cells are likely to be a target for carcinogens resulting in the development of carcinomas (Morris, 1986). Finally, the accessibility of skin makes human KSCs an ideal vehicle for genetic manipulation and gene therapy for the treatment of both skin disorders and systemic deficiencies. The ability to identify and isolate these cells represents an important prerequisite for the development of these approaches.

Telomerase activity

Figure 8:
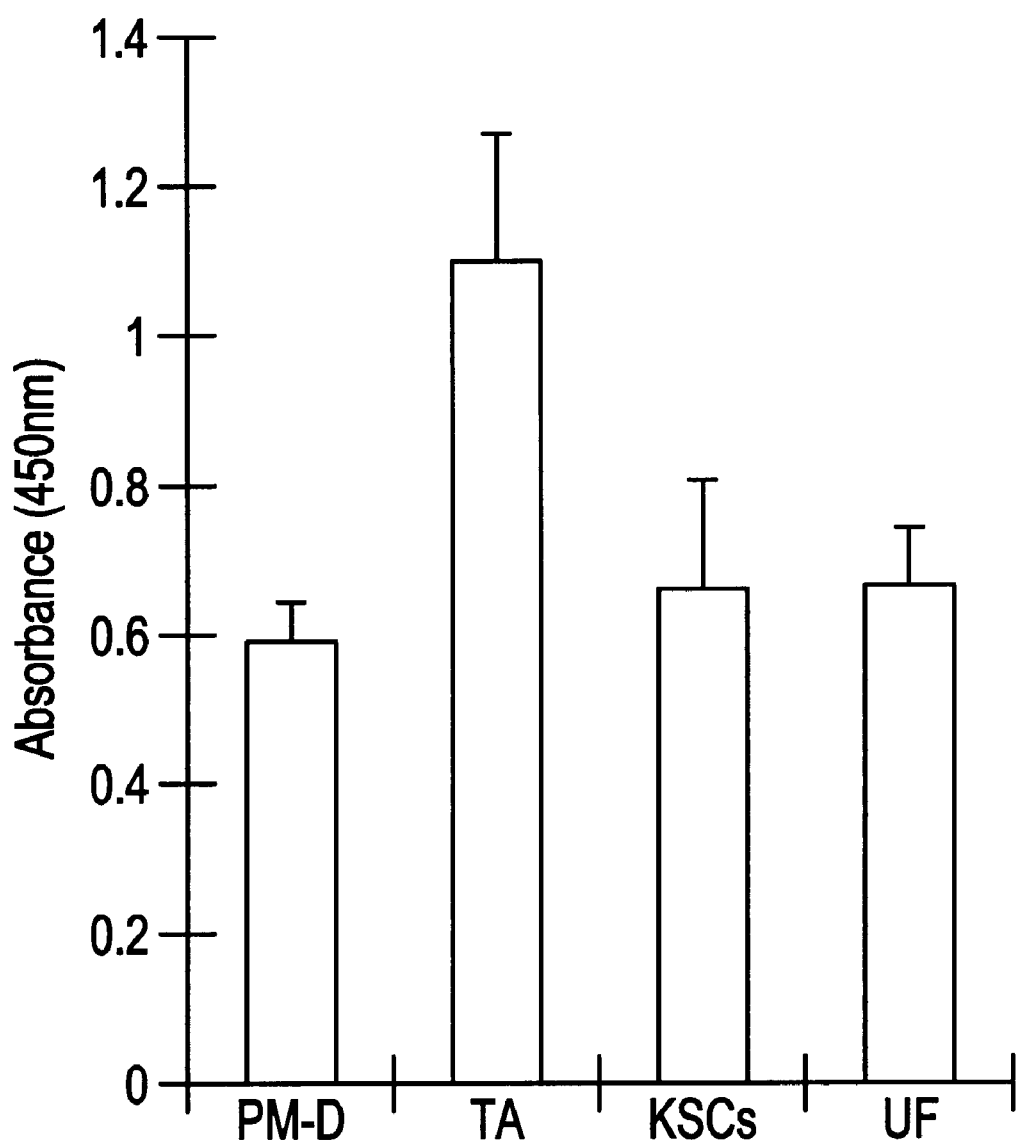
FIG. 8: Is a graphical representation of telomerase activity in fractionated human keratinocytes, as measured by absorbance at 450 nm using an ELISA assay (Kim et al, 1994). PM-D refers to Post-mitotic differentiating cells, TA refers to transit amplifying cells, KSCs refers to keratinocyte stem cells, and UF refers to unfractionated cells.

This ribonucleoprotein enzyme replaces telomeric (chromosome end) nucleotide repeat sequences which are normally lost from the ends of chromosomes with replication. Telomerase activity has been round to be present in a great number of actively proliferating cells including tumour and normal cell lines in culture, and its is now well accepted that there is a good correlation between proliferative cells and telomerase activity (Greider, 1998). It was originally proposed that stem cells which are long lived may contain high levels of telomerase enzyme although it has become evident that haemopoietic committed progenitors (the actively proliferating cells) have relatively high levels of this enzyme, while minimal to undetectable levels are present within the stern cells (Hiyama et al. 1995). Consistent with this data, we have found that KSCs as defined by us as cells with the phenotype $\alpha 6^{bri}10G7^{dim}$ express significantly lower levels of telomerase compared to the actively proliferating TA population (phenotype $\alpha_6 10g7^{bri}$) as shown in FIG. 8. These experiments utilized a TRAP assay telomerase activity as described by Kim et al, (1994) detected by ELISA. The interpretation we favour is that telomerase activity is not essential in normally quiescent stem cells, but is activated during cell cycling.

Adult KSC phenotype

Figure 9:
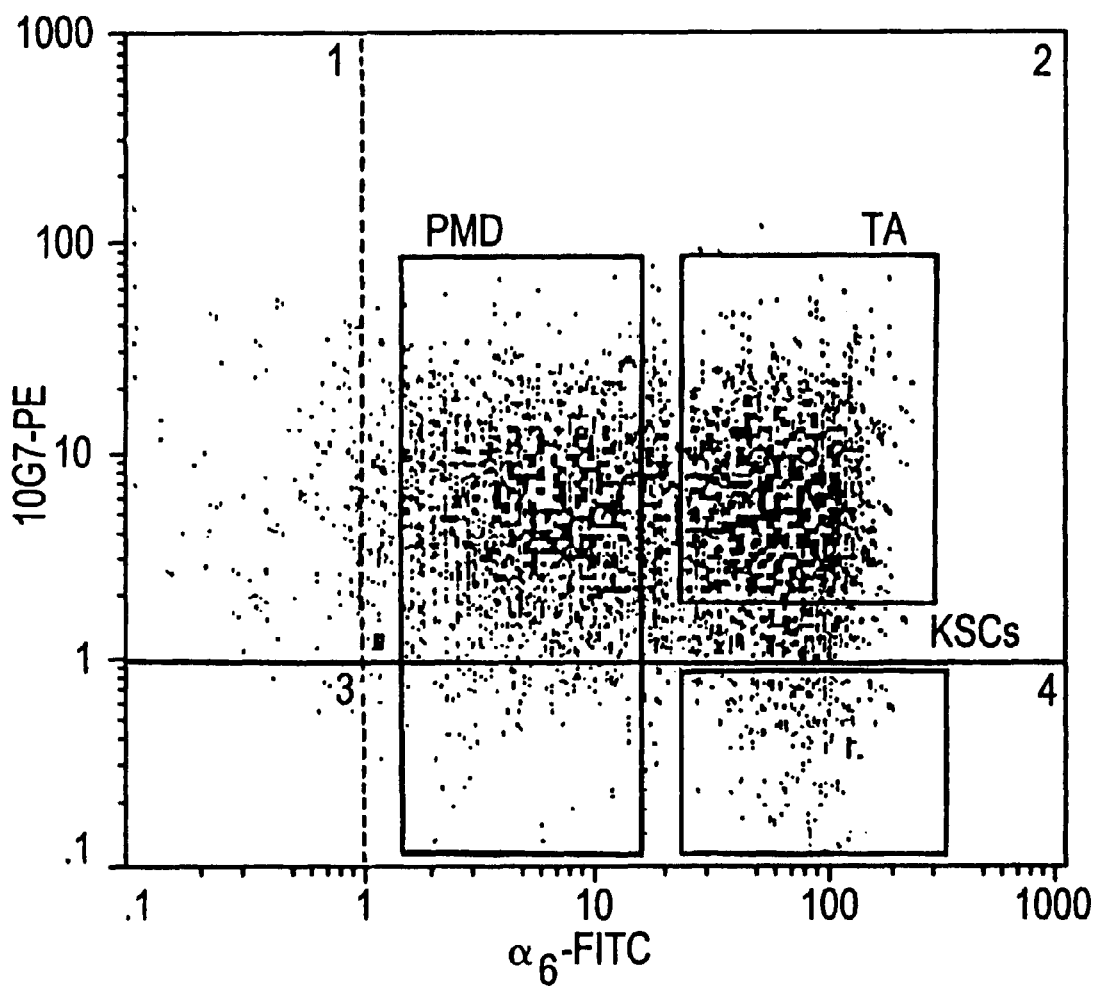
FIG. 9: Is a similar plot to that shown in FIG. 4 except that the cells harvested were from the facial skin of a 72 year old adult. What is shown is a dot plot showing flow cytometric analysis of freshly isolated basal keratinocytes double-labelled with anti-$\alpha_6$ Mab 4F10 (FITC), and Mab 10G7 (PE), from a representative experiment. PM-D refers to Post-mitotic differentiating cells ($\alpha_6^{dim}$), TA refers to transit amplifying cells ($\alpha_6^{bri}10G7^{bri}$) and KSCs refers to keratinocyte stem cells($\alpha_6^{bri}10G7^{dim}$) This phenotype has been observed in numerous replicate experiments. The populations of cells which are similar to those observed in neonatal epidermis are indicated in the boxes.

We have investigated whether the phenotypically distinct populations described by us in neonatal skin tissue are also present in adult epidermis. All three populations present in neonatal epidermis were also found in a number of adult skin samples isolated from people of varying age and taken from various body sites. Importantly, cells of the stem cell phenotype were present in all adult skin samples examined, an example of which is shown in FIG. 9.

EXAMPLE 2

The ability to regenerate epithelium in vivo is an important property of KSCs, and an important prerequisite to the development of gene therapeutic approaches aiming to deliver gene products from skin grafts. This proposed example includes the steps of taking purified KSCs to generate epidermal tissue, which can then be utilised to graft onto individuals.

It is proposed to determine the ability of KSCs to reconstitute an epidermis in the living skin equivalent model of organotypic cultures, a number of these systems are presently being used. This in vitro model system has been extensively used to study the effects of various factors on keratinocytes to proliferate and differentiate into a normal multilayered epidermis and exhibit appropriate gene expression. Basal keratinocytes fractionated into the candidate KSC and TA subpopulations as described earlier may be placed in the organotypic culture system. The cultures can be analysed for morphological and biochemical characteristics to determine the capacity of these KSCs to form epidermal tissue in vivo, with appropriately regulated expression of epidermal differentiation markers. Cultures can be processed for sectioning and immunohistochemical analysis for various epithelial markets including integrins, keratins, involucrin, filaggrin etc. Organotypic cultures will be generated from fractionated basal epidermal cells, (together with unfractionated cells as controls), from both adult and neonatal skin. It is postulated that only the $\alpha_6^{bri}10G7^{dim}$ fraction will be capable of generating a normal epithelium with a basal layer and differentiated layers, and that the $\alpha_6^{dim}$ (and perhaps $\alpha_6^{bri}10G7^{bri}$) fraction will give rise to terminally differentiated cells.

REFERENCES

Allen & Potten (1974) *J. Cell Sci.* 15, 291–319 (1974).
Baum et al (1992) *Proc. Natl. Acad. Sci.* 89, 2804–2808.
Berenson et al. (1991) *Blood* 77, 1717–1722.
Bickenbach et al (1986) *Cell Tissue Kinet.* 19, 325–333.
Carter et al (1990a) *J. Cell Blot.* 110, 1387–1404.
Carter et al (1990b) *J. Cell Biol.*111, 3141–3154.
Christophers (1971) *J. Invest. Dermatol.* 56, 165–169.
Civin et al. (1984) *J. Immunol.* 133, 57–165.
Dowling et al (1996) *J. Cell Biol.*134, 559–572.
Fuchs & Green (1980) *Cell* 19, 1033–1042.
Georges-Labouesse et al (1996) *Nature Genet.* 13, 370–373.

Grieder *Proc Natl Acad Sci* 95: 90–92 (1998)
Haylock et al (1992) *Blood* 80 1405–1412.
Haylock et al. (1997) *Blood* 90, 2260–2272.
Hiyama et al *J. Immunol* 155; 3711–3715.
Hurlin et al (1991) *Proc. Natl. Acad. Sci* 88, 570–574.
Jones et al (1995) *Cell* 80, 83–93.
Jones & Watt (1993) *Cell* 73, 713–724.
Kaur et al. (1997) *J Invest. Dermatol*, 109, 194–199.
Kim et al (1994) *Science* 226, 2011–2015
Lajtha (1979) *Differentiation* 14, 23–34.
MacKenzie & Bickenbach (1985) *Cell Tissue Res.* 242, 551–556.
Mackenzie et al (1989) *Differentiation* 41, 127–138.
Morris et al. (1985) *J. Invest. Dermatol* 84, 277–281.
Morris (1986) *Cancer Res.* 46, 3061–3066.
Morris & Potten (1994) *Cell Proliferation* 27, 279–289.
Peltonen et al (1989) *J. Clin Invest.* 84, 916–1923.
Potten & Hendry (1973) *Int. J. Radiat. Biol.* 24 537–540.
Potten (1983) Stem cells in epidermis from the back of the mouse. In 'Stem Cells: Their identification and characterization', C. S. Potten, eds. (London: Churchill Livingston), p200232.
Potten (1986) *Int. J. Radiat Biol.* 49, 257–278.
Rheinwald & Green (1975) *Cell* 6, 331–344.
Schofield et al (1978) *Blood Cells* 4, 7–25.
Schweizer (1984) *Cell* 37, 159–170.
Sonnenberg et al (1991) *J. Cell Biol.*113, 907–917.
Spangrude et al (1988) *Science* 241, 58–62.
Sutherland et al (1990) *Proc. Natl. Acad Sci. USA.* 87, 3584–3588.
Terstappen et al (1991) *Blood* 77, 1218–1227.
Van-der-Neut et al (1996) *Nature Genet.* 13, 366–369.

What is claimed is:

1. A method of enriching for a viable subpopulation of epidermal cells having an altered proliferative potential compared with an unfractionated population of epidermal cells, wherein said subpopulation is keratinocyte stem cells (KSC) or transit amplifying (TA) cells, said method comprising the steps of:
   (a) harvesting a population of epidermal cells,
   (b) enriching the population resulting from step (a) for cells expressing a higher level of a cell surface integrin compared with an unfractionated population of epidermal cells, wherein said integrin comprises a subunit selected from the group consisting of $\alpha_2$, $\alpha_3$, $\alpha_6$, $\beta_1$, and $\beta_4$, and
   (c) enriching the population resulting from step (b) for cells expressing either a lower level or a higher level of a marker associated with proliferation compared with an unfractionated population of epidermal cells, wherein said marker is selected from the group consisting of transferrin receptor, epidermal growth factor receptor, insulin growth factor receptor and keratinocyte growth factor receptor, thereby enriching for said viable subpopulation of epidermal cells.

2. The method of enriching for a viable subpopulation of epidermal cells as in claim 1, wherein said subpopulation is KSC, and wherein in step (c) the population resulting from step (b) is enriched for cells that express said lower level of said marker associated with proliferation.

3. The method of enriching for a viable subpopulation of epidermal cells as in claim 1, wherein said subpopulation is TA cells, and wherein in step (c) the population resulting from step (b) is enriched for cells that express said higher level of said marker associated with proliferation.

4. The method of enriching for a viable subpopulation of epidermal cells as in claim 1, wherein the epidermal cell population is derived from a skin tissue sample, and wherein prior to step (a) said method comprises a step of separating epidermis from the skin tissue sample.

5. The method of enriching for a viable subpopulation of epidermal cells as in claim 1, wherein the cell surface integrin comprises integrin $\beta_1$.

6. The method of enriching for a viable subpopulation of epidermal cells as in claim 1, wherein the cell surface integrin is $\alpha_6\beta_4$.

7. The method of enriching for a viable subpopulation of epidermal cells as in claim 1, wherein the marker associated with proliferation is the transferrin receptor.

8. The method of enriching for a viable subpopulation of epidermal cells as in claim 1, wherein the enriching for cells expressing said higher level or lower level of either the integrin or the marker associated with proliferation is achieved using a binding agent.

9. A purified epidermal subpopulation isolated by the method of claim 1.

10. The method of enriching for a viable subpopulation of epidermal cells as in claim 2, wherein the method comprises,
   a first enriching step of enriching for cells that express said higher level of said cell surface integrin from the population of epidermal cells to form a partially enriched pool; and
   a second enriching step of removing cells that express said higher level of said marker associated with proliferation from the partially enriched pool.

11. The method of enriching for a viable subpopulation of epidermal cells as in claim 3, wherein the method comprises,
   a first enriching step of enriching for cells that express said higher level of said cell surface integrin from the population of epidermal cells to form a partially enriched pool; and
   a second enriching step of removing cells that express said lower level of said marker associated with proliferation from the partially enriched pool.

12. The method of enriching for a viable subpopulation of epidermal cells as in claim 5, wherein the surface integrin is selected from the group consisting of integrin $\alpha_2\beta_1$ and integrin $\alpha_3\beta_1$.

13. The method of enriching for a viable subpopulation of epidermal cells as in claim 6, wherein a level of the $\alpha_6$ subunit is determined.

14. The method of enriching for a viable subpopulation of epidermal cells as in claim 8, wherein the binding agent is an antibody or fragment thereof.

15. The method of enriching for a viable subpopulation of epidermal cells as in claim 8, wherein the binding agent is a ligand for said integrin or said marker associated with proliferation.

16. A purified KSC population having a purity of greater man 50%.

17. A purified KSC population comprising cells that (i) express a higher level of a cell surface integrin compared with an unfractionated population of epidermal cells, wherein said integrin comprises a subunit selected from the group consisting of $\alpha_2$, $\alpha_3$, $\alpha_6$, $\beta_1$ and $\beta_4$, and (ii) express a lower level of a marker associated with proliferation compared with an unfractionated population of epidermal cells, wherein said marker is selected from the group consisting of transferrin receptor, epidermal growth factor receptor, insulin growth factor receptor and keratinocyte growth factor receptor.

18. The purified KSC population as in claim 17, wherein the surface integrin includes integrin subunit $\beta_1$.

19. The purified KSC population as in claim 17, wherein the cell surface integrin is $\alpha_6\beta_4$.

20. The purified KSC population as in claim 17, wherein the marker associated with proliferation is the transferrin receptor.

21. A composition comprising the purified KSC population of claim 17, and a tissue layer.

22. A composition formed by culturing the purified KSC population of claim 17.

23. A skin graft cultured from a purified KSC population according to claim 17.

24. The purified KSC population as in claim 18, wherein the surface integrin is selected from the group consisting of integrin $\alpha_6\beta_1$ and integrin $\alpha_3\beta_1$.

25. A purified TA cell population comprising cells that (i) express a higher level of cell surface integrin compared with an unfractionated population of epidermal that cells, wherein said integrin comprises a subunit selected from the group consisting of $E_2$, $\alpha_3$, $\alpha_6$, $\beta_1$, and $\beta_4$, and (ii) express a higher level of a marker associated with proliferation compared with an unfractionated population of epidermal cells, wherein said marker is selected from the group consisting of transferrin receptor, epidermal growth factor receptor, insulin growth factor receptor and keratinocyte growth factor receptor.

26. The purified TA cell population as in claim 25, wherein the surface integrin includes integrin subunit $\beta_1$.

27. The purified TA cell population as in claim 25, wherein the cell integrin is $\alpha_6\beta_4$.

28. The purified TA cell population as in claim 25, wherein the marker associated with proliferation is the transferrin receptor.

29. A composition comprising the purified TA cell population of claim 25, and a tissue layer.

30. A composition formed by culturing the purified TA cell population of claim 25.

31. A skin graft cultured from a purified TA population according to claim 25.

32. The purified TA cell population as in claim 26, wherein the surface integrin is selected from the group consisting of integrin $\alpha_2\beta_1$ and integrin $\alpha_3\beta_1$.

* * * * *